United States Patent
Skinner et al.

(10) Patent No.: US 6,908,875 B2
(45) Date of Patent: Jun. 21, 2005

(54) ORGANOMETALLIC COMPOSITIONS AND POLYISOCYANATE COMPOSITIONS CONTAINING THEM

(75) Inventors: Christopher J Skinner, Rue Royale (BE); Martin G Partridge, Eaglescliffe (GB)

(73) Assignee: Acma Limited, Cheshire (GB)

( * ) Notice: Subject to any disclaimer, the term of this patent is extended or adjusted under 35 U.S.C. 154(b) by 221 days.

(21) Appl. No.: 10/060,341

(22) Filed: Feb. 1, 2002

(65) Prior Publication Data

US 2002/0188047 A1 Dec. 12, 2002

Related U.S. Application Data

(63) Continuation of application No. PCT/GB00/02820, filed on Jul. 21, 2000.

(30) Foreign Application Priority Data

Aug. 3, 1999 (GB) ............................................. 9918117

(51) Int. Cl.$^7$ ........................... B01J 31/00; B01J 37/00; C08F 4/02; C08F 4/60
(52) U.S. Cl. ....................... 502/102; 502/103; 556/138; 522/23; 528/55; 528/56; 528/59
(58) Field of Search .................. 502/102, 103; 556/138; 522/23; 528/55, 56, 59

(56) References Cited

U.S. PATENT DOCUMENTS

| | | | | |
|---|---|---|---|---|
| 2,933,462 A | | 4/1960 | Fischer | |
| 4,871,854 A | | 10/1989 | Oberth et al. | |
| 4,935,488 A | * | 6/1990 | Omatsu et al. | 528/272 |
| H1388 H | * | 12/1994 | Matlack | 69/45 |
| 5,418,288 A | * | 5/1995 | Kawasaki et al. | 525/71 |
| 5,521,254 A | * | 5/1996 | Willis | 525/314 |
| 5,567,793 A | * | 10/1996 | Slack et al. | 528/69 |
| 5,597,872 A | * | 1/1997 | Willis | 525/314 |
| 5,633,317 A | * | 5/1997 | Kawasaki et al. | 525/66 |
| 5,644,010 A | * | 7/1997 | Kurihashi et al. | 526/273 |
| 5,663,272 A | * | 9/1997 | Slack et al. | 528/69 |
| 5,686,042 A | * | 11/1997 | Slack et al. | 264/328.6 |
| 5,733,945 A | | 3/1998 | Simpson | |
| 6,063,864 A | * | 5/2000 | Mathur et al. | 525/44 |
| 6,544,651 B2 | * | 4/2003 | Wong et al. | 428/413 |
| 2001/0056166 A1 | * | 12/2001 | Mohri et al. | |

FOREIGN PATENT DOCUMENTS

| | | |
|---|---|---|
| JP | 11080291 | 3/1999 |
| WO | 9513323 | 5/1995 |
| WO | 9717388 | 5/1997 |

* cited by examiner

Primary Examiner—David Sample
Assistant Examiner—Jennine Brown
(74) Attorney, Agent, or Firm—Mayer, Brown, Rowe & Maw, LLP

(57) ABSTRACT

An organometallic composition, suitable for use in curing polyisocyanate compositions, includes a complex of at least one metal selected from iron, cobalt and aluminum and at least one β-dicarbonyl compound wherein when the metal is iron (II) or cobalt (II) the molar ratio of β-dicarbonyl compound to metal is in the range from 2.1:1 to 10:1, and when the metal is aluminum (III), iron (III) or cobalt (III) the molar ratio of β-dicarbonyl compound to metal is in the range from 3.1:1 to 10:1. A polyisocyanate composition containing the organometallic composition and a process for binding lignocellulosic material is also described.

13 Claims, No Drawings

ORGANOMETALLIC COMPOSITIONS AND POLYISOCYANATE COMPOSITIONS CONTAINING THEM

This application is a continuation of International Application PCT/GB 00/02820 filed Jul. 21, 2000, which designated the U.S. and that International Application was published under PCT Article 21(2) in English. The PCT application is hereby incorporated in its entirety by reference.

This invention relates to novel organometallic compositions and polyisocyanate compositions containing them and, in particular, to organometallic compositions based on iron or aluminium and which are useful in polyisocyanate compositions for binding lignocellulosic material.

The use of organic polyisocyanates as binders for lignocellulosic material in the manufacture of sheets or moulded bodies such as waferboard, chipboard, fibreboard and plywood is well known. In a typical process the organic polyisocyanate, optionally in the form of a solution, dispersion or aqueous emulsion, is applied to the lignocellulosic material which is then subjected to heat and pressure.

Suitable polyisocyanate compositions are disclosed in PCT Application WO 97/17388 and our co-pending UK Application GB 9815029.5. These compositions comprise a Group IVB metal compound, preferably a titanium chelate, optionally in combination with a compatibilising compound and/or conventional release agents. Although these compositions perform well as binders for lignocellulosic material and provide good release performance, it is desirable to develop alternative compositions which provide at least as good stability on storage before use, together with good curing properties and excellent bonding strength when applied to the lignocellulosic material.

GB-A-951949 describes the use of metal chelates, including chromium, vanadyl and ferric acetylacetonate as catalysts for the preparation of non-cellular polyurethanes for use as rocket propellants. There is however no description of the storage stability of isocyanate compositions containing these materials or of any of the compositions now found to be beneficial in the preparation of polyisocyanate compositions.

The use of various metal acetylacetonates as catalysts for the isocyanate-hydroxyl group reaction to form a urethane group has been discussed by J. W. Britain, (I & EC Product Research and Development, vol1, no 4, (December 1962) at page 261–264). There is, however, no indication that compositions of the present invention may be beneficial in such applications.

It has now been surprisingly found that certain compositions prepared from β-dicarbonyl compounds can be used to prepare polyisocyanate compositions which are very stable on prolonged storage and economical when used for binding lignocellulosic material.

According to one aspect of the invention an organometallic composition, suitable for use in curing polyisocyanate compositions, comprises a complex of at least one metal selected from the group consisting of iron, aluminium and cobalt and at least one β-dicarbonyl compound wherein, when the metal is iron (II) or cobalt (II), the molar ratio of β-dicarbonyl compound to metal is in the range from 2.1:1 to 10:1, and when the metal is aluminium (III) iron (III) or cobalt (III), the molar ratio of β-dicarbonyl compound to metal is in the range from 3.1:1 to 10:1.

Also according to the invention, a polyisocyanate composition comprises an organometallic composition, said organometallic composition being a complex of at least one metal selected from the group consisting of iron, aluminium and cobalt and a β-dicarbonyl compound wherein, when the metal is iron (II) or cobalt (II), the molar ratio of β-dicarbonyl compound to metal is in the range from 2.1:1 to 10:1, and when the metal is aluminium (III), iron (III) or cobalt (III) the molar ratio of β-dicarbonyl compound to metal is in the range from 3.1:1 to 10:1.

The iron, aluminium or cobalt composition of the invention, suitable for use in a polyisocyanate composition, is described herein as a "complex". It is a feature of this invention that some of the β-dicarbonyl compound will be chemically bound to the metal (Fe, Al or Co) but that some can be described as "free". The exact proportions which are bound and free will depend partly upon the exact molar ratios present in the complex, which metal is used and in which oxidation state the metal is in, but it has been shown that the "free" ester does influence the properties, particularly the stability on storage, or a polyisocyanate composition as a binder for lignocellulosic materials. The use of the word "complex" does not imply that said complex is necessarily separately prepared before addition to a polyisocyanate to form the polyisocyanate compositions of the invention. The complex can be formed in the course of preparing the inventive polyisocyanate composition using alternative methods as described hereinafter.

The β-dicarbonyl compound used to prepare the complexes of the invention can be any suitable β-dicarbonyl compound. Preferred β-dicarbonyl compounds include diketones, for example acetylacetone (2,4-pentanedione), benzoyl acetone, dibenzoylmethane, 2,2,6,6-tetramethylheptanediene and 1,1,1-trifluoro-2,4-pentanedione and esters of acetoacetic acid such as ethylacetoacetate, methylacetoacetate, isopropylacetoacetate and tertiarybutylacetoacetate. A complex may be based on one β-dicarbonyl compound but particularly useful complexes have been prepared from a mixture of β-dicarbonyl compounds such as a mixture or acetylacetone and ethylacetoacetate.

The molar ratio of β-dicarbonyl compound to metal the complex is from greater than the oxidation state of the metal up to 10. Preferably, the molar ratio is preferably in the range 3.5 1 to 8:1 and more preferably in the range 5:1 to 8:1. In agreement with conventional theories about the co-ordination chemistry of iron (II) and cobalt (III) complexes, two molecules of the β-dicarbonyl compound will be chemically bound to the metal atom and any remaining will be "free", and for aluminium (III), iron (III), and cobalt (III) complexes, three molecules of the β-dicarbonyl compound will be chemically bound to the metal atom and any remaining will be "free".

Typically, the complexes of iron, cobalt or aluminium may be prepared from the alkoxide, condensed alkoxide, hydroxide, halide or other compounds by methods known to those skilled in the art. For example, aluminium complexes may be prepared directly from the metal, the metal tri-alkyl, or more preferably from the alkoxide or halide by reaction with β-dicarbonyl compound. Iron complexes may also be derived from alkoxides. Typical alkoxides have the general formula $M(OR)_x$ in which M is Al or Fe, x is the oxidation state of the metal, i.e. 2 or 3, and R is a substituted or unsubstituted, cyclic or linear, alkyl, alkenyl, aryl or alkylaryl group or mixtures thereof. Preferably, R contains up to 8 carbon atoms and, more preferably, up to 6 carbon atoms. Generally, all OR groups are identical but alkoxides derived from a mixture of alcohols can be used and mixtures of alkoxides can be employed when more than one metal is present in the complex. Suitable alkoxides include trimethoxyaluminium, trimethoxyiron, triethoxyaluminium, triethoxyiron, tri-isopropoxyaluminium, tri-isopropoxyiron, tri-n-propoxyaluminium, tri-n-propoxyiron, tritertiarybutoxy-aluminium, tritertiarybutoxyiron, tri-sec-butoxyaluminium and tri-sec-butoxyiron. Iron and cobalt complexes are preferably prepared for example from the halide by direct reaction of the metal compound with the β-dicarbonyl compound in the presence of a base or from the hydroxide. Metathesis reactions whereby the complex is prepared from an iron, cobalt or aluminium compound, usually but not always a halide, and a salt, usually but not always the sodium, potassium, lithium or magnesium salt of the β-dicarbonyl compound, are also suitable for preparing complexes of the present invention.

The aluminium complex can be readily prepared by mixing, for example, an alkoxide or condensed alkoxide with an appropriate amount of β-dicarbonyl compound. Alcohol from the alkoxide will be displaced by the β-dicarbonyl compound and, preferably, the displaced alcohol is removed by, for example, distillation. In a preferred method, 3 moles of β-dicarbonyl compound (e.g. acetyacetone) per atom of Al are added to an alkoxide or condensed alkoxide and the displaced alcohol is removed by distillation. Additional β-dicarbonyl compound is then added to the stripped product. This method is advantageous because it provides a consistent product of known stoichiometry. The iron or cobalt complexes can readily be prepared by generating a reactive hydroxide treatment of the metal chloride in water with ammonia and reacting this with β-dicarbonyl compound.

In one method of preparing the polyisocyanate compositions of the invention, a product containing 2 or 3 moles of β-dicarbonyl compound per Co, Fe or Al atom can be mixed with additional β-dicarbonyl compound to produce the complex of the invention and this complex can be added to a polyisocyanate composition. For aluminium complexes, a product containing 1 mole of β-dicarbonyl compound per Al atom is a suitable starting material for this method. Alternatively, the product containing 2 or 3 moles of β-dicarbonyl compound per Co, Fe or Al atom can be prepared and any additional β-dicarbonyl compound required to produce the polyisocyanate composition of the invention can be added to the polyisocyanate before or after the iron or aluminium compound has been added. Other methods of preparing the composition of the invention will be apparent to a person skilled in this art.

A further metal complex may be present in the organometallic composition, for example a complex of titanium, zirconium or hafnium may be present in addition to the Co, Fe or Al complex. Such a complex may, for example, comprise a complex of at least one of titanium, zirconium or hafnium and at least one of an acetoacetate ester or alkoxide. As an example, a complex of the general formula $Ti(OR)_2(EAA)_2$ may be present, where R is a substituted or unsubstituted, cyclic or linear, alkyl, alkenyl, aryl or alkylaryl group or mixtures thereof and EAA is ethylacetoacetate.

The amount of iron, aluminium or cobalt complex present in the polyisocyanate composition of the invention is usually in the range 0.01 to 20% by weight, based on the polyisocyanate and, preferably, the amount is in the range 0.1 to 10%. More preferably, the amount of complex present is in the range 0.2 to 7% by weight with respect to polyisocyanate and, frequently, acceptable curing can be achieved if the amount of complex present is in the range 0.2 to 2% by weight with respect to polyisocyanate.

Polyisocyanates or use in the polyisocyanate composition of the present invention may be any organic polyisocyanate compound or mixture of organic polyisocyanate compounds, provided said compounds nave at least 2 isocyanate groups. Organic polyisocyanates include diisocyanates, particularly aromatic diisocyanates, and isocyanates of higher functionality.

Examples of organic polyisocyanates which may be used in the composition of the present invention include aliphatic isocyanates such as hexamethylene diisocyanate; and aromatic isocyanates such as m- and p-chenylene diisocyanate, tolylene-2,4-and tolylene-2,6-diisocyanate, diphenylmethane-4,4'-diisocyanate, chlorophenylene-2,4-diisocyanate, napnthylene-1,5-diisocyanate, diphenylene-4,4'-diisocyanate,4,4'-diisocyanate 3,3'-dimethyl-diphenyl, 3-methyldiphenylmethane-4,4'-diisocyanate and diphenyl ether diisocyanate; and cycloaliphatic diisocyanates such as cyclohexane-2,4- and cyclohexane-2,3-diisocyanate, 1-methylcyclohexyl-2,4- and 1-methyl-cyclohexyl-2,6-diisocyanate and mixtures thereof and bis-(isocyanato-cyclohexyl)methane and triisocyanates such as 2,4,6-triisocyanatotoluene and 2,4,4-triisocyanatodiphenylether.

Modified polyisocyanates containing isocyanurate, carbodiimide or uretonimine groups may be employed as well. Further, blocked polyisocyanates, like the reaction product of a phenol or an oxime and a polyisocyanate, may be used, having a deblocking temperature below the temperature applied when using the polyisocyanate composition.

The organic polyisocyanate may also be an isocyanate-ended prepolymer made by reacting an excess of a diisocyanate or higher functionality polyisocyanate with a polyol. Water-emulsifiable organic polyisocyanates like those described in UK patent no. 1 444 933, in European patent publication no. 516 361 and in PCT patent publication no. 91/03082 can also be used.

Mixtures of isocyanates may be used, for example a mixture of toluiene diisocyanate isomers such as the commercially available mixtures of 2,4- and 2,6-isomers and also the mixture of di- and higher poly-isocyanates. Polyisocyanate mixtures may optionally contain monofunctional isocyanates such as p-ethyl phenylisocyanate. Such mixtures are well-known in the art and include the crude phosgenation products containing methylene bridged polyphenyl polyisocyanates, including diisocyanate, triisocyanate and higher polyisocyanates together with any phosgenation by-products.

Preferred isocyanates to be used in the present invention are those wherein the isocyanate is an aromatic diisocyanate or polyisocyanate of higher functionality such as a pure diphenylmethane diisocyanate or a mixture of methylene bridged polyphenyl polyisocyanates containing diisocyanates, triisocyanates and higher functionality polyisocyanates.

Methylene bridged polyphenyl polyisocyanates are well known in the art. They may be prepared by phosgenation of corresponding mixtures of polyamines. For convenience, polymeric mixtures of methylene bridged polyphenyl polyisocyanates containing diisocyanate, triisocyanate and higher functionality polyisocyanates are referred to hereinafter as polymeric MDI. Suitable polyisocyanates include SUPRASEC™ DNR, SUPRASEC™ 2185,RUBINATE™ M and RUBINATE™ 1840, all available from Huntsman Polyurethanes.

Preferably the polyisocyanate is liquid at room temperature.

Conventional release agents can be added to or used in combination with the polyisocyanate composition of the present invention containing an iron or aluminum complex of a β-dicarbonyl compound.

The conventional release agent is present in an amount varying between 0.2 and 10%, preferably between 0.5 and 6% and most preferably between 1 and 3% by weight based on the polyisocyanate whereas the iron or aluminium complex of a β-dicarbonyl compound is preferably present in an amount varying between 0.2 and 4%, most preferably between 0.2 and 2% by weight based on the polyisocyanate.

Examples of conventional release agents include polysiloxanes, saturated or unsaturated fatty acids (such as oleic acid) or fatty acid amides or fatty acid esters and polyolefin waxes.

Preferred conventional release agents to be used according to the present invention are polyolefin waxes or mixtures of polyolefin waxes, especially functionalised polyolefin waxes, which are dispersible in an aqueous medium to form an aqueous emulsion. More preferably, the polyolefin waxes are selected from oxidised polyethylene waxes and oxidised polypropylene waxes.

A preferred method for using the release agent is to apply the emulsion to the surface of the polyisocyanate treated lignocellulosic material or to the press metal surface prior to hot pressing the combination.

When used, the aqueous emulsion of the polyolefin wax should normally contain a sufficient amount of the polyolefin wax to provide a coverage of about 0.01 to about 1, and preferably about 0.02 to about 0.5 mg of the polyolefin wax per $cm^2$ of lignocellulosic material or press metal surface. Generally, lower levels of polyolefin wax are preferred as they are more cost effective. When taking the emulsifiers into account, the aqueous emulsions will usually contain about 0.2 to about 10%, preferably about 0.3 to about 5% by weight of total solids. The emulsions are usually prepared at 30 to 40% total solids, transported to the point of use and then diluted with water to the desired concentration.

It has been found that the polyolefin wax emulsion, when used in combination with polyisocyanate compositions of the present invention, may be usefully applied to the lignocellulosic material or press metal surface in an amount equivalent to 8 to 14 mg per $cm^2$ A particularly preferred polyethylene wax emulsion which can be used in a process in combination with a polyisocyanate composition of the present invention is Rubilon™ 603 or Rubilon™ 605, both available From Huntsman Polyurethanes. A particularly preferred polypropylene wax emulsion which can be used in the present process is ME 42040 available from Michelman Inc. of Cincinnati, Ohio.

In order to further improve the storage stability of the polyisocyanate composition of the present invention a diluent may be added to the composition. Suitable diluents include plasticizers of the type mentioned in "Taschenbuch der Kunststoff-Additive", Ed. by R. Gachter and H. Muller, Carl Hanser Verlag München. third edition, 1989. Preferred diluents are phthalates, aliphatic carboxylates, fatty acid esters, linseed oil and soybean oil. A particularly preferred diluent is Priolube 1403 available from Unichema being methyl oleate. These diluents are added in amounts of from 1 to 40 parts by weight per 100 parts by weight of polyisocyanate and preferably in amounts of from 1 to 15 parts by weight per 100 parts by weight of polyisocyanate.

The composition further may comprise conventional additives like flame retardants, lignocellulosic preserving agents, fungicides, waxes, sizing agents, fillers, surfactants, thixotropic agents and other binders like formaldehyde condensate adhesive resins and lignin (optionally in combination with a lignin solvent such as described in PCT Patent Application No. EP96/00924).

A particularly preferred additive to be used in the polyisocyanate composition of the present invention is a coupling agent such as an organofunctional silane (for example, Dynasylan AMEO, available from Huels). Adding such a coupling agent to the polyisocyanate composition leads to improved board properties. The organofunctional silane coupling agents are used in amounts ranging from 0.01 to 3%, preferably from 0.1 to 2% by weight based on the polyisocyanate.

The polyisocyanate composition of the present invention can be made by simply mixing the ingredients at room temperature.

The present invention is also concerned with a process for preparing lignocellulosic bodies by bringing lignocellulosic parts into contact with the present polyisocyanate composition and by pressing this combination.

Therefore the present invention also provides a process for binding lignocellulosic material comprising the steps of
a) bringing said lignocellulosic material in contact with the polyisocyanate composition according to one embodiment of this invention and
b) subsequently allowing said material to bind.

The lignocellulosic bodies are prepared by the lignocellulosic parts into contact with the polyisocyanate composition by means such as mixing, spraying and/or spreading the composition with/onto the lignocellulosic parts and by pressing the combination of the polyisocyanate composition and the lignocellulosic parts, preferably by hot-pressing, typically at 150° C. to 250° C. and 2 to 6 MPa specific pressure. Such binding processes are commonly known in the art.

In waferboard manufacture the lignocellulosic material and the polyisocyanate composition may be conveniently mixed by spraying the present polyisocyanate composition on the lignocellulosic material while it is being agitated.

As described hereinbefore, in a preferred process according to the invention, a release agent, which is preferably an aqueous emulsion of a polyolefin wax, is applied to the surface of the polyisocyanate treated lignocellulosic material or to the press metal surface prior to hot pressing the combination.

The lignocellulosic material after treatment with the polyisocyanate composition is placed on plates made of aluminium or steel which serve to carry the furnish into the press where it is compressed to the desired extent usually at a temperature between 150° C. and 250° C.

While the process is particularly suitable for the manufacture of waferboard known also as oriented strand board and will be largely used for such manufacture, the process may not be regarded as limited in this respect and can also be used in the manufacture of medium density fiberboard, particle board (also known as chipboard) and plywood. Thus the lignocellulosic material used can include wood strands, woodchips, wood fibres, shavings, veneers, wood wool, cork, bark, sawdust and like waste products of the wood working industry as well as other materials having a lignocellulosic basis such as paper, bagasse, straw, flax, sisal, hemp, rushes, reeds, rice hulls, husks, grass, nutshells and the like. Additionally, there may be mixed with the lignocellulosic materials other particulate or fibrous materials such as ground foam waste (for example, ground polyurethane foam waste), mineral fillers, glass fibre, mica, rubber, textile waste such as plastic fibres and fabrics.

When the polyisocyanate composition is applied to the lignocellulosic material, the weight ratio of polyisocyanate/lignocellulosic material will vary depending on the bulk density of the lignocellulosic material employed. Therefore, the polyisocyanate compositions may be applied in such amounts to give a weight ratio of polyisocyanate/ lignocellulosic material in the range of 0.1:99.9 to 20:80 and preferably in the range of 0.5:99.5 to 10:90.

If desired other conventional binding agents, such as formaldehyde condensate adhesive resins, may be used in conjunction with the polyisocyanate composition.

More detailed description of methods of manufacturing waferboard and similar products based on lignocellulosic material are available in the prior art. The techniques and equipment conventionally used can be adapted for use with the polyisocyanate compositions of the present invention.

The polyisocyanate compositions of the present invention are extremely effective in minimising unwanted adhesion to caul plates, press plates and other surfaces with which the treated lignocellulosic material may come into contact. Their storage stability and release performance is improved compared to polyisocyanate compositions of the prior art, as well as the obtained board properties. The sheets and moulded bodies produced from the polyisocyanate compositions of the present invention have excellent mechanical properties and they may be used in any of the situations where such articles are customarily used.

The invention is illustrated but not limited by the following examples.

EXAMPLE 1

Preparation of Aluminium tris(acetylacetonate)

To a flask containing 50 g of a mixture of heptane isomers was added 30.8 g (0.125 mol) of Al tris(sec-butoxide). To this was added with stirring 37.55 g (0.375 mol) of acetylacetone. After stirring, a white precipitate of aluminium tris(acetylacetonate) was collected and washed on a filter paper. Yield=36.6 g (91%).

Preparation of Iron tris(acetylacetonate)

20.3 g of anhydrous iron (III) chloride (0.124 mol) was dissolved in 30 g of demineralised water with gentle warming. To this was added 45 ml of ammonia solution (SG. 0.880). The mixture was then heated on a steam bath for 30 minutes. The precipitate of iron (III) hydroxide was filtered and washed free of chloride. The moist iron (III) hydroxide and 60 g of acetylacetone (0.6 mol) were mixed together and heated for 30 minutes. Crystals of Fe(acac)$_3$ were deposited and were recrystallised from ethanol.

TABLE 1A

| Sample | Metal | Moles EAA added* |
|---|---|---|
| 1A (comp) | Fe | 0 |
| 1B | Fe | 0.5 |
| 1C | Fe | 2.0 |
| 1D | Fe | 4.0 |
| 1E (comp) | Al | 0 |
| 1F | Al | 0.5 |
| 1G | Al | 2.0 |
| 1H | Al | 4.0 |

TABLE 1B

| Sample | Metal | Moles acac added* |
|---|---|---|
| 1J-(comp) | Fe | 0 |
| 1K | Fe | 0.5 |
| 1L | Fe | 2.0 |
| 1M | Fe | 4.0 |
| 1N-(comp) | Al | 0 |
| 1O | Al | 0.5 |

TABLE 1B-continued

| Sample | Metal | Moles acac added* |
|---|---|---|
| 1P | Al | 2.0 |
| 1Q | Al | 4.0 |

*per mole metal tris(acetylacetonate)

Complexes were prepared by mixing the metal acetylacetonates prepared as above with ethylacetoacetate (EAA) or acetyl acetone (acac) in various molar ratios, as shown in Tables 1A and 1B. Control samples having no added β-dicarbonyl compound were included.

The samples were evaluated by preparing, at 25° C., duplicate compositions comprising 100 parts by weight of polyisocyanate (polymeric MDI, Suprasec DNR, available from Huntsman Polyurethanes) and between 0.23 and 0.6 parts of the samples designated 1A to 1Q wherein in every case the quantity of metal (iron or aluminium) added was 0.706 mmol. The compositions were then stored at 45° C. and the viscosity tested, at 25° C., by means of a Brookfield viscometer at various intervals. The average results are given in Tables 2A and 2B below [all viscosities are in Pa·s].

TABLE 2A

| Time | Sample | | | | | | | |
|---|---|---|---|---|---|---|---|---|
| (Days) | 1A | 1B | 1C | 1D | 1E | 1F | 1G | 1H |
| 0 | 202 | 202 | 202 | 202 | 202 | 202 | 202 | 202 |
| 10 | 474 | 250 | 250 | 262 | 344 | 224 | 216 | 220 |
| 21 | 1030 | 376 | 300 | 334 | 425 | 251 | 256 | 242 |
| 70 | 3602 | 978 | 542 | 509 | 615 | 536 | 266 | 258 |
| 94 | 6448 | 1736 | 704 | 732 | 880 | 406 | 352 | 308 |

TABLE 2B

| Time | Sample | | | | | | | |
|---|---|---|---|---|---|---|---|---|
| (Days) | 1J | 1K | 1L | 1M | 1N | 1O | 1P | 1Q |
| 0 | 244 | 244 | 244 | 244 | 244 | 244 | 244 | 244 |
| 18 | 348 | 296 | 312 | 320 | 932 | 536 | 362 | 392 |
| 44 | 392 | 330 | 372 | 396 | 1763 | 868 | 536 | 574 |
| 60 | 490 | 380 | 418 | 448 | 3138 | 1288 | 994 | 984 |

Generally, the most relevant period for storage stability at room temperature is the period 14 to 46 days after production of the polyisocyanate composition. From Tables 2A and 2B it can be seen that iron and aluminium complexes of the invention used in polyisocyanate compositions of provide an economical means of stabilising the composition over the un-complexed tris(acetylacetonate) compounds.

EXAMPLE 2

Preparation and Testing of Aluminum tris(ethylacetoacetate) Complexes

To a flask containing 50.02 g of a mixture of heptane isomers was added 31.0 g (0.125 mol) of aluminium tris (sec-butoxide). To this was added with stirring, 48.37 g (0.376 mol) of ethylacetoacetate. After stirring the liquor was transferred to a rotary evaporator flask and the volatile sec-butanol and heptanes (78.66 g) were removed under vacuum leaving aluminium tris(ethylacetoacetate) (51.23 g, 0.124 mol).

Samples of aluminium tris(ethylacetoacetate) prepared as above was mixed with additional ethylacetoacetate as indicated in Table 3 below.

TABLE 3

| Sample | Moles EAA added* |
|---|---|
| 2A-(comp) | 0 |
| 2B | 0.5 |
| 2C | 4.0 |

*per mole of Al(EAA)$_3$

The samples were evaluated by preparing, at 25° C., duplicate compositions comprising 100 parts by weight of polyisocyanate (polymeric MDI, Suprasec DNR, available from Huntsman Polyurethanes) and between 0.29 and 0.66 parts of the samples designated 2A–2C wherein in every case the quantity of metal (aluminium) added was 0.706 mmol. The compositions were then stored at 45° C. and the viscosity tested, at 25° C., by means of a Brookfield viscometer at various intervals. The average results are given in Table 4 below [all viscosities are in Pa·s]. The results show that EAA complexes with Al(EAA)$_3$ to provide improved storage stability in isocyanate compositions

TABLE 4

| Time | Sample | | |
|---|---|---|---|
| (days) | 2A | 2B | 2C |
| 0 | 224 | 224 | 224 |
| 10 | 272 | 236 | 234 |
| 20 | 310 | 258 | 252 |
| 49 | 324 | 256 | 274 |
| 73 | 510 | 290 | 418 |

EXAMPLE 3
Preparation and Testing of Iron tris(acetylacetonate)/ethylacetoacetate Complex A sample of an organometallic complex was prepared by mixing 1 mole of iron tris(acetylacetonate), as prepared in Example 1 with 2.5 moles ethylacetoacetate. The sample was evaluated by preparing, at 25° C., a composition comprising 100 parts by weight of polyisocyanate (polymeric MDI. Rubinate 1840. available from Huntsman Polyurethanes) and 0.48 parts of the sample. The composition was then stored at 45° C. and the viscosity tested, at 25° C., by means of a Brookfield viscometer at various intervals. Results are given in Table 5 below [all viscosities are in Pa·s].

TABLE 5

| | Time (days) | | | | |
|---|---|---|---|---|---|
| | 0 | 20 | 40 | 65 | 100 |
| Viscosity (Pas) | 220 | 290 | 300 | -20 | 620 |

EXAMPLE 4

An organometallic complex was prepared by mixing 2.5 g of iron tris(acetylacetonate), obtained from the Sigma-Aldrich Company Limited, with 2.3 g ethylacetoacetate in a flask with stirring.

The organometallic complex (0.48 parts) was mixed with 100 parts by weight of polyisocyanate (polymeric MDI, SUPRASEC DNR, available from Huntsman Polyurethanes). This composition was used to prepare single layer boards of aspen at 2.5% and 6% resin based on dry wood. Boards of 12×450×450 mm and density 650 kg/m$^3$ were made using the above composition and also containing a sizing wax emulsion (SPG 60 available from Condea Chemie) at 1% loading (solid wax) based on dry wood. The prepressing moisture content was 8%. For comparison, similar boards were prepared using the polyisocyanate without the organometallic complex (Comparison).

Composites were then prepared using the following pressing conditions:

| Press Close (Contact position): | 50 s |
|---|---|
| Cure Time: | 10 s/mm |
| Degas Time: | 15 s |
| Press Temperature: | 200° C. |

The composites produced under conditions described above were then tested using a range of industry standard tests to measure physical properties (Modulus of elasticity and rupture according to EN310; Swelling after 24 hrs of soaking in water according to EN317). Results are given in Table 6 below.

The measured properties showed no significant performance difference between composites prepared with SUPRASEC DNR alone and when the product of Example 4 was present. This demonstrates the utility of using polyisocyanate compositions containing compositions of the invention to produce composites without affecting physical performance of the resulting composite panels.

TABLE 6

| | 2.5% Binder loading | | | | 6% Binder loading | | |
|---|---|---|---|---|---|---|---|
| Property | Example 4 | SD | Comparison | SD | Example 3 | SD | Comparison |
| Modulus of Elasticity (%) | 4562 | 797 | 4993 | 431 | 5345 | 1129 | 5113 |
| Modulus of Rupture (%) | 34.9 | 9.0 | 35.5 | 5.8 | 44.5 | 12.7 | 43.5 |
| Thickness Swell (%) | 16.5 | 1.6 | 17.0 | 3.3 | 10.6 | 1.0 | 7.8 |

EXAMPLE 5

Boards were made using a polyisocyanate comprising different parts by weight of the organometallic complex of Example 4 and 100 parts by weight of standard polyisocyanate SUPRASEC DNR—see Table 7). The release performance of the boards was tested. In order to reproduce the failure mode all spray of release agent was stopped from the 7th repeat onwards. It is considered that a release rating (see below) of 3 will cause a catastrophic failure under largescale manufacturing conditions. The release trials were run in parallel and for each composite the release from the top and bottom platten was measured. The per cent wood failure (amount of the platten covered by residual wood) was also recorded. Results are summarised in Tables 8 and 9 below.

Composites were prepared using the following pressing conditions:

| Press Close (Contact position): | 20 s |
|---|---|
| Cure Time: | 9.3 s/mm |
| Degas Time: | 20 s |
| Press Temperature: | 170° C. |

TABLE 7

| Sample | Weight percent Example 4 product | Release agent (g/m$^2$) |
|---|---|---|
| 5A | 0 | 4 |
| 5B | 0.48 | 2 |
| 5C | 0.32 | 2 |
| 5D | 0.32 | 1 |

The release rating is given a value from 1 to 5 having the following significance:

1 complete sticking, board can not be removed without destruction of the board 2 stacking with wood failure higher than 50%

3 sticking with wood failure less than 25% but higher than 5%

4 sticking with wood failure less than 5%. Little force needed to remove board.

4.5 sticking without wood failure, hanging board. No effort needed to remove board.

5 perfect release, the board releases spontaneously.

The results shown in Tables 8 and 9 show that a composition containing an organometallic complex of the invention improves the performance of a system using an external release agent and allows this performance to be maintained as the level of external release agent is significantly reduced.

TABLE 8

| No. of re-peats | Release Rating 5A Top | 5A Bottom | % Wood Failure 5A Top | 5A Bottom | Release Rating 5B Top | 5B Bottom | % Wood Failure 5B Top | 5B Bottom |
|---|---|---|---|---|---|---|---|---|
| 1 | 4.5 | 5 | 0.5 | 5 | 5 | 5 | 0 | 0 |
| 2 | 5 | 4.5 | 0.5 | 7 | 5 | 5 | 0 | 0 |
| 3 | 5 | 4 | 2 | 10 | 5 | 5 | 0 | 0 |
| 4 | 5 | 4.5 | 3 | 10 | 5 | 5 | 0 | 0 |
| 5 | 5 | 5 | 3 | 10 | 5 | 5 | 0 | 0 |
| 6 | 5 | 4 | 1 | 12 | 5 | 5 | 0 | 0 |
| 7 | 5 | 4 | 2 | 15 | 5 | 5 | 0 | 0 |
| 8 | 4.5 | 5 | | | 5 | 5 | | |
| 9 | 4.5 | 5 | | | 5 | 5 | | |
| 10 | 4.5 | 5 | 2 | 15 | 4.5 | 5 | 0 | 0.5 |

TABLE 9

| No. of re-peats | Release Rating 5C Top | 5C Bottom | % Wood Failure 5C Top | 5C Bottom | Release Rating 5D Top | 5D Bottom | % Wood Failure 5D Top | 5D Bottom |
|---|---|---|---|---|---|---|---|---|
| 1 | 5 | 5 | 0 | 0 | 5 | 5 | 0 | 0 |
| 2 | 5 | 5 | 0 | 0 | 5 | 5 | 0 | 0 |
| 3 | 5 | 5 | 0 | 0 | 5 | 5 | 0 | 0.5 |
| 4 | 5 | 5 | 0 | 0 | 5 | 5 | 0 | 0 |
| 5 | 5 | 5 | 0 | 0 | 5 | 5 | 0 | 0 |
| 6 | 5 | 4.5 | 0 | 0 | 4.5 | 5 | 0 | 0 |
| 7 | 5 | 4.5 | 0 | 0 | 5 | 5 | 0 | 0 |
| 8 | 5 | 5 | | | 4.5 | 5 | | |
| 9 | 4.5 | 5 | | | 5 | 5 | | |
| 10 | 4 | 5 | 0.5 | 0 | 4.5 | 5 | 0 | 0 |

EXAMPLE 6

Testing of Cobalt tris(acetylacetonate)/ (Co(acac$_3$)) Complexes

Samples of cobalt tris(acetylacetonate) obtained from the Sigma-Aldrich Company Limited were mixed with ethylacetoacetate (EAA) in molar ratios between 1:0.5 and 1:4 (cobalt tris(acetylacetonate): β-dicarbonyl compound). The samples were evaluated by preparing, at 25° C., duplicate compositions comprising 100 parts by weight of polyisocyanate (polymeric MDI. Suprases DNR, available from Huntsman Polyurethanes) and between 0.25 and 0.62 parts of the mixed samples made up as shown in Table 10 wherein in every case the quantity of metal (cobalt) added was 0.706 mmol. The compositions were then stored at 45° C. and the viscosity tested, at 25° C., by means of a Brookfield viscometer at various intervals. Average results are given in Table 10 below [all viscosities are in Pa s].

TABLE 10

| Moles EAA added* | Days | | | |
|---|---|---|---|---|
| | 0 | 19 | 43 | 60 |
| 0 (comp) | 244 | 268 | 251 | 292 |
| 0.5 | 244 | 274 | 256 | 302 |
| 2.0 | 244 | 256 | 256 | 266 |
| 4.0 | 244 | 252 | 256 | 272 |

*per mole Co tris(acetylacetonate)

The results show that EAA complexes with cobalt tris (acetylacetonate) to provide improved storage stability in isocyanate compositions

EXAMPLE 7

Preparation and Testing of Iron tris (tetramethylheptanedionate) (Fe(TMHD)$_3$) Complexes Iron tris(tetramethylheptanedionate) was mixed with ethylacetoacetate (EAA) in molar ratios between 1:0.5 and 1:4 (Fe(TMHD)$_3$: β-dicarbonyl compound. The samples were evaluated by preparing at 25° C., duplicate compositions comprising 100 parts by weight of polyisocyanate (polymeric MDI, Suprasec DNR, available from Huntsman Polyurethanes) and between 0.43 and 0.79 parts of the mixed samples made up as shown in Table 11 wherein in every case the quantity of metal (iron) added was 0.706 mmol. The compositions were then stored at 45° C. and the viscosity tested, at 25° C., by means of a Brookfield viscometer at various intervals. Average results are given in Table 11 below [all viscosities are in Pa s].

TABLE 11

|  | Moles EAA | Days | | |
| --- | --- | --- | --- | --- |
|  |  | 0 | 31 | 55 |
| Fe(TMHD)$_3$ | 0 (comp) | 212 | 236 | 338 |
| Fe(TMHD)$_3$ | 0.5 | 212 | 240 | 224 |
| Fe(TMHD)$_3$ | 1.0 | 212 | 230 | 214 |
| Fe(TMHD)$_3$ | 2.0 | 212 | 236 | 212 |
| Fe(TMHD)$_3$ | 4.0 | 212 | 244 | 272 |

The results show that EAA complexes with Fe(TMHD)$_3$ to provide improved storage stability in isocyanate compositions

EXAMPLE 8

Preparation and Testing of Iron tris(benzoylacetone)(Fe(BzAc)$_3$ Complexes

Iron tris(benzoylacetone) was mixed with ethylacetoacetate (EAA) in molar ratios between 1:0.5 and 1:4 (Fe(BzAc)$_3$:β-dicarbonyl compound). The samples were evaluated by preparing, at 25° C., duplicate compositions comprising 100 parts by weight of polyisocyanate (polymeric MDI, Suprasec DNR, available from Huntsman Polyurethanes) and between 0.38 and 0.75 parts of the mixed samples made up as shown in Table 12 wherein in every case the quantity of metal (iron) added was 0.706 mmol. The compositions were then stored at 45° C. and the viscosity tested, at 25° C., by means of a Brookfield viscometer at various intervals. Average results are given in Table 12 below [all viscosities are in Pa s].

TABLE 12

|  | Moles EAA | Days | | | |
| --- | --- | --- | --- | --- | --- |
|  |  | 0 | 20 | 49 | 63 |
| Fe(BzAc)$_3$ | 0 (comp) | 240 | 270 | 290 | 320 |
| Fe(BzAc)$_3$ | 0.5 | 240 | 266 | 279 | 330 |
| Fe(BzAc)$_3$ | 1.0 | 240 | 270 | 263 | 302 |
| Fe(BzAc)$_3$ | 2.0 | 240 | 290 | 286 | 348 |
| Fe(BzAc)$_3$ | 4.0 | 240 | 314 | 354 | 386 |

The results show that Fe(BzAc)$_3$ itself provides a storage-stable isocyanate composition and that β-dicarbonyl compound may be added to effect a change in stability.

EXAMPLE 9

Preparation and Testing of Mixed Ti/Fe and Ti/Al Complexes

A mixture was prepared of iron tris(acetylacetonate), and di(isopropoxy)titanium bis(ethylacetoacetate), having an equal number of moles of iron and titanium and containing an additional 2.5 moles of EAA per mole of titanium plus iron. A similar mixture was also prepared using di(isopropoxy)titanium bis(ethylacetoacetate) and Al(acac)$_3$. Shelf life tests were performed as before using 0.5 g of these mixtures per 100 g of polyisocyanate. The results are shown in Table 14.

The results show that combining Ti and Fe or Al can provide improved control over the storage stability of catalyst-polyisocyanate compositions.

TABLE 13

| Al(acac)$_3$ | Fe(acac)$_3$ | Ti(OiPr)$_2$(EAA)$_2$ | EAA | Days | | | |
| --- | --- | --- | --- | --- | --- | --- | --- |
| (moles) | (moles) | (moles) | (moles) | 0 | 15 | 44 | 60 |
| 0.5 | — | 0.5 | 2.5 | 244 | 354 | 476 | 542 |
| — | 0.5 | 0.5 | 2.5 | 244 | 382 | 524 | 584 |
| — | — | (Comparison) | 2.5 | 244 | 406 | 564 | 656 |

What is claimed is:

1. An organometallic composition, suitable for use in curing polyisocyanate compositions, comprising:
   a) a complex of at least one metal selected from the group consisting of iron, aluminium and cobalt;
   b) a β-discarbonyl compound selected from benzoyl acetone, dibenzoylmethane, 2,2,6,6-tetramethylheptanedione, 1,1,1-trifluoro-2,4-pentanedione, or a β-ketoester; and
   c) optionally, a second β-dicarbonyl compound;
   wherein, when the metal is iron (II) or cobalt (II), the molar ratio of total β-dicarbonyl compound to metal is in the range from 2.1:1 to 10:1, and when the metal is aluminium (III) iron (III) or cobalt (III), the molar ratio of total β-dicarbonyl compound to metal is in the range from 3.1:1 to 10:1.

2. An organometallic composition according to claim 1, wherein the molar ratio of total β-dicarbonyl compound to metal is in the range 3.5:1 to 8:1.

3. An organometallic composition according to claim 1, wherein the second β-dicarbonyl compound is a β-diketonate or a β-ketoester.

4. An organometallic composition according to claim 3, wherein the second β-dicarbonyl compound is selected from acetylacetone, benzoyl acetone, dibenzoylmethane, 2,2,6,6-tetramethylheptanedione, 1,1,1-trifluoro-2,4-pentanedione, ethylacetoacetate, methylacetonacetate, isopropylacetoacetate or teriarybutylacetoacetate.

5. An organometallic composition according to claim 1, wherein the composition comprises one β-dicarbonyl compound.

6. An organometallic composition according to claim 1, wherein the composition comprises more than one β-dicarbonyl compound.

7. An organometallic composition according to claim 1, wherein the complex is prepared by reacting an alkoxide or condensed alkoxide of aluminium with one or more β-dicarbonyl compound.

8. An organometallic composition according to claim 1, wherein the complex is prepared by reacting a halide, hydroxide or salt of iron, cobalt or aluminium with one or more β-dicarbonyl compound.

9. The organometallic composition of claim 1 further comprising at least one polyisocyanate.

10. The organometallic composition of claim 9 wherein said at least one polyisocyanate is diphenylmethane diisocyanate or a mixture of methylene bridged polyphenyl polyisocyanates.

11. The organometallic composition of claim 9 further comprising a release agent in an amount in the range 0.2 to 10 wt. %.

12. The organometallic composition of claim 11 wherein said release agent is a polysiloxane, a fatty acid, a fatty acid amide, a fatty acid ester or a polyolefin wax.

13. The organometallic composition according to claim 9 further comprising a diluent.

* * * * *